US012691132B2

(12) United States Patent
Tanaka et al.

(10) Patent No.: US 12,691,132 B2
(45) Date of Patent: Jul. 28, 2026

(54) SPERM MOTILITY IMPROVING AGENT AND SPERM MOTILITY IMPROVING METHOD

(71) Applicants: MIRAILAB BIOSCIENCE INC., Tokyo (JP); HIROSHIMA UNIVERSITY, Hiroshima (JP)

(72) Inventors: Megumi Tanaka, Tokyo (JP); Tsunemaru Tanaka, Tokyo (JP); Masayuki Shimada, Tokyo (JP)

( * ) Notice: Subject to any disclaimer, the term of this patent is extended or adjusted under 35 U.S.C. 154(b) by 461 days.

(21) Appl. No.: 18/044,089

(22) PCT Filed: Sep. 7, 2021

(86) PCT No.: PCT/JP2021/032772
§ 371 (c)(1),
(2) Date: Mar. 6, 2023

(87) PCT Pub. No.: WO2022/054778
PCT Pub. Date: Mar. 17, 2022

(65) Prior Publication Data

US 2023/0321127 A1 Oct. 12, 2023

(30) Foreign Application Priority Data

Sep. 8, 2020 (JP) ................................ 2020-150259

(51) Int. Cl.
*A61K 31/706* (2006.01)
*A61K 31/4745* (2006.01)
*A61P 15/08* (2006.01)

(52) U.S. Cl.
CPC ........ *A61K 31/706* (2013.01); *A61K 31/4745* (2013.01); *A61P 15/08* (2018.01)

(58) Field of Classification Search
CPC .................................................... A61K 31/706
USPC ........................................................... 514/52
See application file for complete search history.

(56) References Cited

U.S. PATENT DOCUMENTS

| | | | | |
|---|---|---|---|---|
| 10,898,738 | B2 * | 1/2021 | Tanaka | A61P 27/10 |
| 11,219,590 | B2 * | 1/2022 | Tanaka | A61K 8/606 |
| 2013/0059384 | A1 * | 3/2013 | Tilly | C07D 495/04<br>435/408 |

FOREIGN PATENT DOCUMENTS

| | | | | |
|---|---|---|---|---|
| CN | 107174583 A | * | 9/2017 | A61K 31/4745 |
| CN | 109350622 A | * | 2/2019 | A61K 8/4926 |
| JP | 2005053783 A | | 3/2005 | |
| JP | 2014520526 A | | 8/2014 | |
| WO | 2018200357 A1 | | 11/2018 | |
| WO | 2020013086 A1 | | 1/2020 | |
| WO | 2020115764 A1 | | 6/2020 | |

OTHER PUBLICATIONS

Strait et al., WashU Medicine News Release—Jan. 7, 2019. (Year: 2019).*
Zhu et al., "A behind the scenes look at the longevity vitamin PQQ", College of Chemistry—UC Berkeley, Jul. 27, 2020 (Year: 2020).*
Youngson et al., Reproduction, 2019, vol. 158(2), pp. 169-179. (Year: 2019).*
European Search Report; Munich; Sep. 17, 2024.
Losano, J. D. A., et al. (2017). The Stimulated Glycolytic Pathway Is Able to Maintain ATP Levels and Kinetic Patterns of Bovine Epididymal Sperm Subjected to Mitochondrial Uncoupling. Oxidative medicine and cellular longevity, 2017, 1682393. https://doi.org/10.1155/2017/1682393.
Zhu, Z., et al. (2019). Negative effects of ROS generated during linear sperm motility on gene expression and ATP generation in boar sperm mitochondria. Free radical biology & medicine, 141, 159-171. https://doi.org/10.1016/j.freeradbiomed.2019.06.018.
Youngson NA, Uddin GM, Das A, et al. Impacts of obesity, maternal obesity and nicotinamide mononucleotide supplementation on sperm quality in mice. Reproduction. 2019; 158(2):169-179. doi:10.1530/REP-18-0574.
Grandhaye J, Partyka A, Ligocka Z, et al. Metformin Improves Quality of Post-Thaw Canine Semen. Animals (Basel). 2020;10(2):287. Published Feb. 12, 2020. doi:10.3390/ani10020287.
Sergiy M. Nadtochiy et al; 234 - Direct Stimulation of Glycolysis Accounts for Cellular Metabolic Benefits of the NAD+ Precursor Nicotinamide Mononucleotide (NMN) Free Radical Biology and Medicine vol. 112, Supplement 1, Nov. 2017, p. 161.
ISR; Japan Patent Office; Jan. 26, 2021.

* cited by examiner

*Primary Examiner* — Traviss C Mcintosh, III
(74) *Attorney, Agent, or Firm* — Patshegen IP; Moshe Pinchas

(57) ABSTRACT

[PROBLEM] To provide a sperm motility improvement agent that is highly safe and may effectively improve sperm motility.
[SOLUTION] A sperm motility improvement agent comprising nicotinamide mononucleotide as an active ingredient.

6 Claims, 3 Drawing Sheets

[Fig. 1]
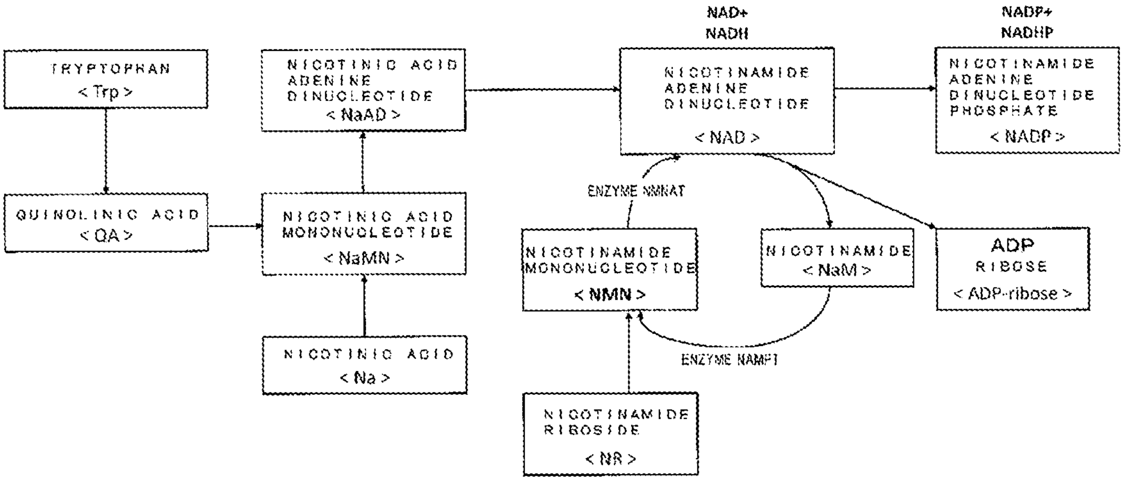
[Fig. 2a]
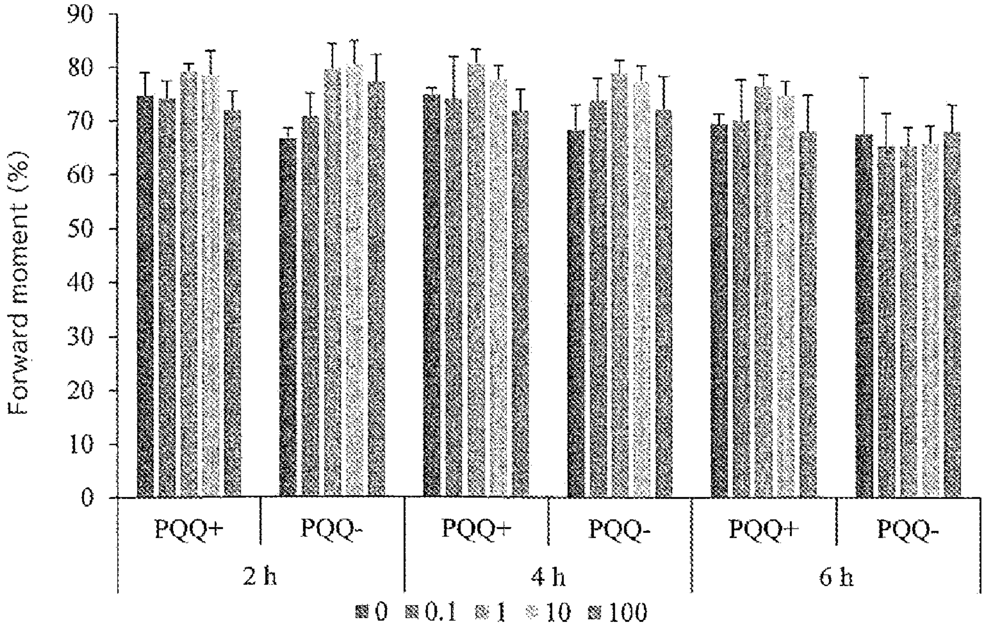

[Fig. 2b]
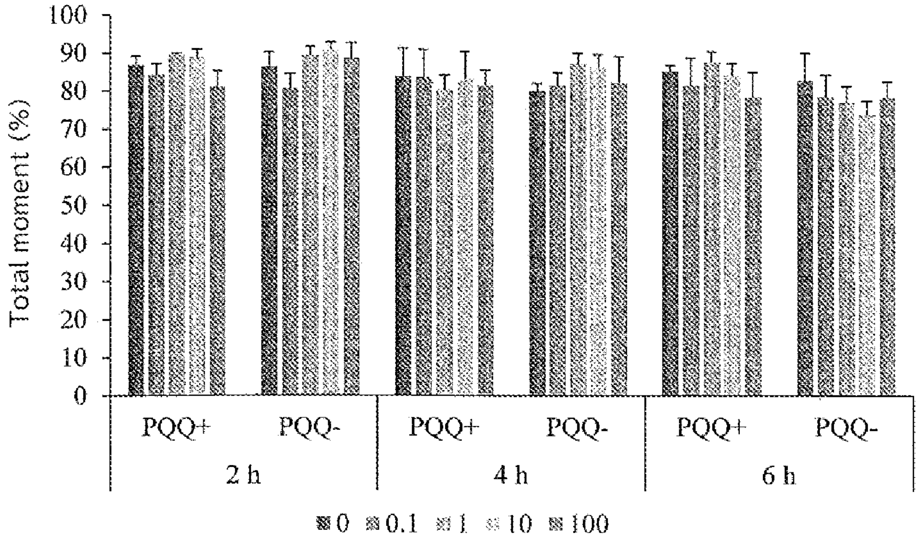
[Fig. 2c]
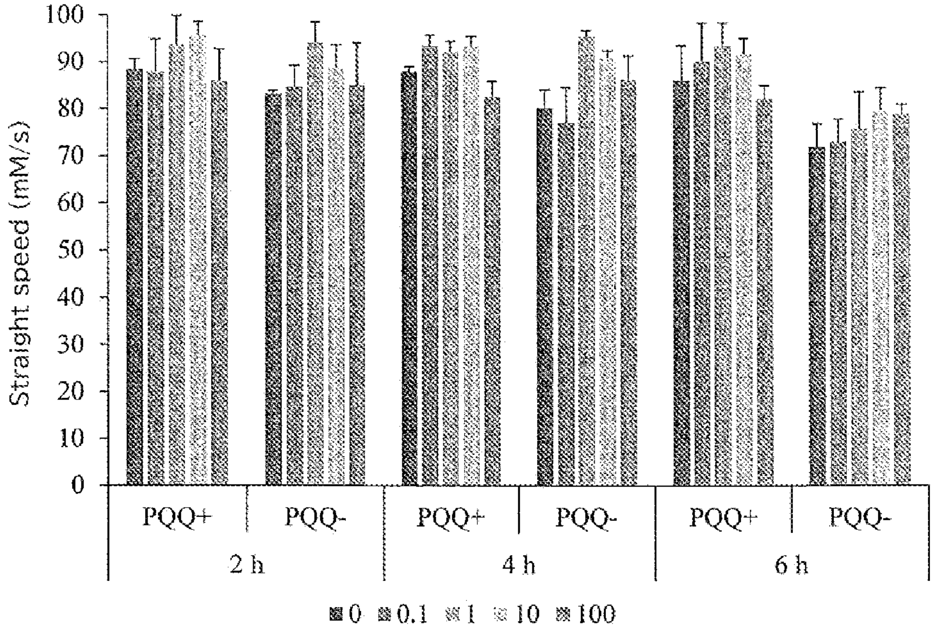

[Fig. 3]
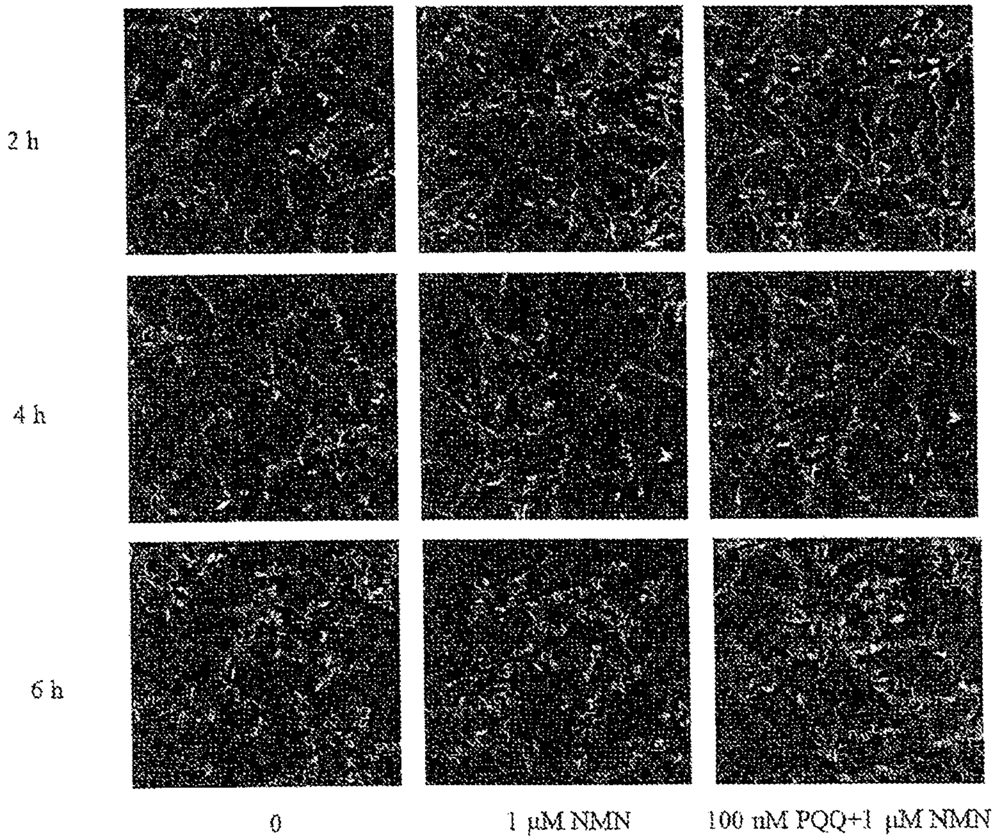

SPERM MOTILITY IMPROVING AGENT AND SPERM MOTILITY IMPROVING METHOD

TECHNICAL FIELD

The present invention relates to a sperm motility improvement agent and method of improving sperm motility.

BACKGROUND ART

Fertilization is the process by which a sperm of a male germ cell fuses with an ovum of a female germ cell and the nuclei of both cells copulate to form a single cell (fertilized ovum). In many mammals, fertilization takes place at an ampulla of uterine tube. Once an ovum is ovulated from an ovary, it is aspirated into a tubal fimbriae and migrates to an ampulla of uterine tube. A sperm, on the other hand, after being ejaculated, travels through the female genital tract such as the uterus and a tuba uterina to reach an ampulla of uterine tube.

Thus, in order for a sperm to fertilize an ovum, a sperm must move within the genital tract in search of an ovum, thus the sperm motility is one of the key factors in determining whether fertilization will take place or not.

A sperm is generally divided into three parts: head, neck, and tail. The tail consists of a single extremely long and developed flagellum (cilium), with microtubules accumulating in its interior under a peculiar arrangement. Mitochondria are accumulated in a coiling manner in the middle part, the beginning of the tail, and provide ATP, the energy for the sperm motion. The sperm motion is then made by shaking the tail while consuming ATP generated by the mitochondria. Specifically describing this motion, it is believed that the structure of dynein, a molecular motor in an axoneme the flagellum, changes as it consumes ATP as energy, which causes sliding motion of the microtubules, which is converted to rippling motion of the flagellum. Then, during fertilization, a sperm receives a variety of external factors around it, from which dynein activity is regulated. The flagellum is composed of peripheral microtubules, dynein, radial spokes, nexin-dynein regulated complex (N-DRC) and the like, which, if not properly formed, result in abnormal flagellum formation and reduced motility capability.

As can be seen from the above description, the sperm motility is a key factor in determining whether fertilization will take place or not. Semen contains a mixture of sperms of various levels in terms of quality, and the condition of these sperms is evaluated by sperm concentration, morphology, and the like, as well as motility. The condition of reduced sperm motility is termed asthenozoospermia and is one of the major causes of infertility due to male factors or a reduced fertilization rate. In humans, semen inspection is done according to the WHO standard manual, and a diagnosis of asthenozoospermia is generally made when there is less than 50% forward motion sperms and less than 25% fast forwarding sperms.

In Japan, the number of couples suffering from infertility is increasing, it is said that one in every 5.5 couples suffers from infertility, and it is estimated that about 500,000 people are undergoing some kind of infertility treatment. And it is becoming clear that about 80% of the cause of infertility caused by the male side is attributable to asthenozoospermia. The cause of asthenozoospermia has been pointed out to be the effects of harmful substances such as environmental hormones, but this is not clearly known currently.

Infertility treatment includes drug therapy such as fertility drugs, tuba uterina insufflation for tuba uterina communication disorder, tuba uterina plasty, vas deferences plasty for vas deferences functional disorder, artificial insemination, in vitro fertilization and the like. In infertility treatment, treatment methods vary depending on the patient's age and disease, and patients undergoing infertility treatment suffer from physical pain, mental depression, financial burdens and the like. And despite the fact that such infertility treatment is being done, there is a problem that the birth rate from infertility treatment is very low in Japan.

In livestock, on the other hand, it is generally judged as asthenozoospermia when less than 50% of sperms show active forward motion at the time of sperms collection. When it is judged as asthenozoospermia, testicular atrophy, inflammation of the testes, accessory gonad or urethra, or urine contamination and the like are suspected as the cause, and treatment involve measures to eliminate the cause of the disease, but prognosis is generally poor. Cattle breeding is carried out by artificial insemination method using cryopreserved sperms from superior bulls (elite bulls), but it is known that the conception rate of cattle (the proportion of cattle that become pregnant out of those were artificially inseminated) has been decreasing year by year. Thus, infertility is a major problem in the livestock world.

In consideration of such circumstances, with respect to moment of sperms that is one of the causes of infertility on the male side, various agents and methods have been developed to improve the sperm motility. In one example, a method for improving sperm motility activity and/or sperm production capability in mammals other than humans in which adipose tissue-derived stromal cell-containing cells obtained by enzymatic treatment of subcutaneous adipose tissues taken from mammals other than humans are administered to mammals other than humans with reduced sperm motility activity and/or sperm production capability (Patent Document 1) has been reported.

In other examples, a pharmaceutical composition for increasing sperm momentum containing oyster and ginseng extracts as active ingredients (Patent Document 2), a sperm motility improvement agent consisting of a gas containing 1 (v/v) % or more molecular hydrogen (Patent Document 3), a sperm activating agent containing protamine (Patent Document 4), a method of promoting sperm motility capability in vitro, including adding a drug composition containing a glycoprotein-containing macromolecular protein that activates sperm motility capability with a molecular mass of 66 kDa and a pharmaceutically acceptable excipient to semen in vitro, thereby improving sperm motility capability related to the treatment of infertility in humans and breeding in livestock (Patent Document 5), etc. has been reported.

PRIOR ART DOCUMENT

Patent Document

PLT 1: JP-A-2017-25038
PLT 2: JP-A-2004-83517
PLT 3: Re-publication of PCT International Publication No. 2015-64109
PLT 4: JP-A-2010-6785
PLT 5: JP-A-H11-279075

DISCLOSURE OF THE INVENTION

Problems to be Solved by the Invention

The problem of the present invention is to provide a sperm motility improvement agent and a method of improving sperm motility that are highly safe and may effectively improve sperm motility.

Solutions to the Problems

As a result of intensive research to solve the above problem, the inventor has found that nicotinamide mononucleotide, an intermediate metabolite involved in the biosynthesis of the coenzyme NAD (nicotinamide adenine dinucleotide), has an excellent sperm motility improving effect, and has completed the present invention.

The present invention is as follows.

[1] A coenzyme Q production accelerator that contains nicotinamide mononucleotide as an active ingredient.

[2] The sperm motility improvement agent according to [1], further comprising pyrrolo-quinoline quinone.

[3] The sperm motility improvement agent according to [1] or [2], wherein the sperm is a mammalian sperm.

[4] The sperm motility improvement agent according to any one of [1] to[3], wherein the nicotinamide mononucleotide is added to semen with a sperm concentration of $5\times10^6$ to $50\times10^6$/ml such that a concentration of the nicotinamide mononucleotide becomes 0.05 to 150 μM.

[5] The sperm motility improvement agent according to any one of [2] to [4], wherein the pyrrolo-quinoline quinone is added to semen with a sperm concentration of $5\times10^6$ to $50\times10^6$/ml such that a concentration of the pyrrolo-quinoline quinone nicotinamide becomes 20 to 200 nM.

[6] The sperm motility improvement agent according to any one of [2] to[5], wherein a molar ratio of the nicotinamide mononucleotide to the pyrrolo-quinoline quinone is 1:1 to 1500:1.

[7] The sperm motility improvement agent according to any one of [1] to [6], wherein the sperm motility improvement agent is a pharmaceutical product for improving sperm motility.

[8] The sperm motility improvement agent according to any one of [1] to [6], wherein the sperm motility improvement agent is food and drink for improving sperm motility.

[9] A method of improving sperm motility, comprising bringing nicotinamide mononucleotide in contact with sperms in vitro or in vivo.

[10] The method according to [9], further comprising bringing pyrrolo-quinoline quinone in contact with sperms in vitro or in vivo.

[11] The method according to [9] or [10], wherein the sperm is a mammalian sperm.

[12] The method according to any one of [9] to [11], comprising adding the nicotinamide mononucleotide to semen with a sperm concentration of $5\times10^6$ to $50\times10^6$/ml such that a concentration of the nicotinamide mononucleotide becomes 0.05 to 150 μM.

[13] The method can further include adding the pyrrolo-quinoline quinone nicotinamide to semen with a sperm concentration of $5\times10^6$ to $50\times10^6$/ml such that a concentration of the pyrrolo-quinoline quinone becomes 20 to 200 nM.

[14] A sperm treated by the method according to any one of [9] to [13].

Effects of the Invention

The present invention may effectively improve the sperm motility, and since nicotinamide mononucleotide, an intermediate metabolite involved in the biosynthesis of NAD+ in vivo, is an active ingredient, it is highly safe and may be applied with confidence.

BRIEF DESCRIPTION OF THE DRAWINGS

FIG. 1 is an explanatory diagram illustrating metabolic pathways related to niacin (general term for nicotinamide and nicotinic acid).

a graph diagram indicating results of Embodiment 1.

FIG. 2*a* is a graph showing the forward moment (%) of said sperms during swine sperms incubation under the conditions of adding NMN alone or NMN+PQQ.

FIG. 2*b* is a graph showing the total moment (%) of said sperms during swine sperms incubation under the conditions of adding NMN alone or NMN+PQQ.

FIG. 2*c* is a graph showing the straight speed (μM/s) of said sperms during swine sperms incubation under the conditions of adding NMN alone or NMN+PQQ.

FIG. 3 is a photograph showing the sperm motion loci during swine sperms incubation under the conditions of adding NMN alone or NMN+PQQ.

DESCRIPTION OF PREFERRED EMBODIMENTS

The sperm motility improvement agent of the present invention has nicotinamide mononucleotide as an active ingredient, and has a sperm motility improving effect. As shown in the working example below, the present invention is particularly effective in increasing the straight moment and the straight speed in the straight motion of sperms, which is essential for sperms to ascend in the genital tract. In the present invention, the sperm motility improvement includes not only the sperm motility improvement in a narrow sense, but also prevention, cessation of progression and retardation of sperm motility reduction.

Nicotinamide mononucleotide as an active ingredient may obtain the action effect of the sperm motility improvement, and the detailed mechanism of the action is currently under investigation, but it is estimated to be as follows. That is, adding nicotinamide mononucleotide to semen increases the amount of NAD/NADH in sperms, activates the electron transfer system, increases ATP concentration in mitochondria. ATP is thought to be the energy source for the sperm motion, causing sliding motion of microtubules due to structural changes in dynein within an axoneme, which is converted to motion of flagellum, thereby enhancing the sperm motility. Hereinafter, the present invention will be described in detail.

The nicotinamide mononucleotide (chemical formula: $C_{11}H_{15}N_2O_8P$) is a compound produced in bodies of many organisms including human, and expressed with a structural formula [Chem. 1] below. The nicotinamide mononucleotide is generally referred to as NMN, and known as an intermediate metabolite involved in a biosynthesis of coenzyme $NAD^+$.

[Chem.1 ]

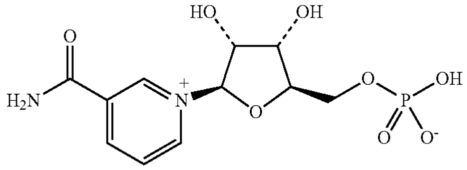

The nicotinamide mononucleotide used as an active agent is produced in an NAD metabolic pathway by liver tissues, that is, a pathway involved in a synthesis of a nicotinamide adenine dinucleotide (NAD) from a quinolinic acid through a kynurenine pathway, in vivo. This will be specifically described with reference to FIG. 1. FIG. 1 is an explanatory drawing illustrating a metabolic pathway involved in niacin (generic term of a nicotinamide and a nicotinic acid) known as vitamin $B_3$. The nicotinic acid ingested through a meal is absorbed by the liver to be converted into nicotinamide, and the nicotinamide is supplied to the whole body via a blood flow. The cells each absorb the nicotinamide from the blood, and convert it into the NAD and an NADP to use them. The nicotinamide is biosynthesized also from a tryptophan.

As illustrated in FIG. 1, in vivo, when the tryptophan is a starting material, the tryptophan is converted into the quinolinic acid (QA) through the kynurenine pathway as a tryptophan metabolic pathway, and further converted into a nicotinic acid mononucleotide (NaMN). Meanwhile, when the nicotinic acid (Na) is the starting material, the nicotinic acid is directly converted into the NaMN. Afterwards, the NaMN is interconverted into the NAD, a nicotinamide (NaM), and the nicotinamide mononucleotide in a NAD cycle through a nicotinic acid adenine dinucleotide (NaAD). The nicotinamide (NaM) is converted into the nicotinamide mononucleotide by a nicotinamide phosphoribosyltransferase (NAMPT), subsequently, the nicotinamide mononucleotide is converted by a nicotinamide mononucleotide adenyltransferase (NMNAT) to generate the NAD. Note that, the nicotinamide mononucleotide is produced also from a nicotinamide riboside (NR) as an NAD intermediate metabolite.

The nicotinamide mononucleotide includes two types of an α-form and a β-form as optical isomers, and the β-form is used in the present invention. The nicotinamide mononucleotide is obtained by, for example, synthesizing a nicotinamide riboside from the nicotinamide and a ribose (see Bioorg. Med. Chem. Lett., 12, 1135-1137 (2002)), and subsequently, phosphorylating a 5-hydroxyl group of the ribose part (see Chem. Comm., 1999, 729-730). Specifically, for example, first, a reaction solution is prepared by dissolving the nicotinamide and an L-ribose tetraacetate in anhydrous acetonitrile, adding a trimethylsilyl trifluorosulfonic acid by an excessive amount under a nitrogen stream and then stirring at room temperature, and adding methanol to stop the reaction. The above-described reaction solution is poured into a column filled with activated carbon, cleaned with a distilled water, and then eluted with methanol and its product is collected. Next, for a phosphorylation reaction of the 5-hydroxyl group of the L-ribose part of this product, a reaction solution is prepared by dissolving the above-described product in a trimethoxy phosphoric acid, dropping a phosphorus oxychloride below freezing and stirring under the nitrogen stream, adding a sodium hydroxide aqueous solution to neutralize, thus stopping the reaction. A cold acetonitrile-ether solution is added to the above-described reaction solution. Afterwards, a lower layer (water phase) is passed through an anion-exchange resin to collect a reactant, and further purifies the reactant with a cation-exchange resin, thus the high-purity nicotinamide mononucleotide can be collected. The nicotinamide mononucleotide is commercially available, and those commercial products can be purchased for use.

The nicotinamide mononucleotide is a purified product that contains a few impurities, especially, preferably its purity is 90% or more, and further preferably its purity is 95% or more. When the purity is less than 90%, a bad smell possibly occurs, or the effect of the nicotinamide mononucleotide is possibly reduced to fail to sufficiently provide the effect of the present invention.

In the sperm motility improvement agent of the present invention, the content of nicotinamide mononucleotide as an active ingredient is not particularly limited. The amount of said sperm motility improvement agent to be used may be determined as appropriate by observing the effect, but in one embodiment, when semen with a sperm concentration (total sperm count) of $5\times10^6$ to $50\times10^6$/ml is as a standard, said sperm motility improvement agent is added so that the concentration of the nicotinamide mononucleotide, the active ingredient contained in said sperm motility improvement agent, is 0.05 to 150 μM, preferably 0.05 to 120 μM, more preferably 1 to 100 μM, based on said semen. When the concentration is less than 0.05 μM, the effect of the present invention may not be obtained, on the other hand, when the concentration exceeds 150 μM, the effect obtained is not so different and economically disadvantageous. In the case where pyrrolo-quinoline quinone below is contained, in one embodiment, when semen with a sperm concentration (total sperm count) of $5\times10^6$ to $50\times10^6$/ml is as a standard, the sperm motility improvement agent is preferably added so that the concentration of the nicotinamide mononucleotide, the active ingredient contained in the sperm motility improvement agent, is 1 to 10 μM, based on said semen.

The sperm motility improvement agent of the present invention is readily manufactured by using nicotinamide mononucleotide alone or by mixing it with other ingredients. The other ingredients are not particularly limited as long as they have the effects of the present invention.

Other ingredients in the present invention that are particularly effective in enhancing its sperm motility improving action include pyrrolo-quinoline quinone (PQQ) (including its salts). According to the presumed mechanism of the present invention described above, adding nicotinamide mononucleotide to semen (bringing it into contact with sperm) increases the amount of NAD/NADH in sperm, activates the electron transfer system, increases ATP concentration in mitochondria, and enhances the sperm motility. However, in this case, when the electron transfer system is activated, the generation of active oxygen (ROS) is also increased, and the active oxygen is expected to have a negative effect on the effect sustainability of nicotinamide mononucleotides. Therefore, as a result of the inventor's consideration of the countermeasures based on this expectation, they found for the first time that the selection and addition of pyrrolo-quinoline quinone in particular, among many antioxidants, may enhance the sustainability of the sperm motility improving effect of nicotinamide mononucleotides.

Pyrrolo-quinoline quinone works as an essential oxidation-reduction coenzyme for the energy acquisition system of living organisms, and has been shown to have many physiological activities, including a function as a vitamin belonging to the vitamin B group and a radical scavenger, a brain function improving action, a neuroprotection action, an enhancing action of nerve growth factors, an antioxidant action, a mitochondrial renewal action, a memory capability improvement action, an identification capability improvement action and the like, and is a compound that is expected to have a wide variety of applications. Pyrrolo-quinoline quinone is widely present in the biological world and is contained in high concentrations in breast milk and in trace amounts in various vegetables and meats. It is contained in a relatively large amount in tea, natto, and fruits in particular.

In the present invention, pyrrolo-quinoline quinone (or its salts) may be its hydrates or solvates. Pyrrolo-quinoline quinone salts include alkali metal salts such as sodium and potassium salts, alkaline earth metal salts such as magnesium and calcium salts, ammonium salt, organic amine salts such as triethanolamine and trimethylamine salts, basic amino acid salts such as lysine and arginine salts, and the like. Pyrrolo-quinoline quinone salts may be used alone or in a mixture.

In one embodiment in the present invention, pyrrolo-quinoline quinone (reduced form) represented by the following structural formula [Chem. 2] is used. Reduced pyrrolo-quinoline quinone is a water-soluble substance obtained by reducing the quinone moiety of oxidized pyrrolo-quinoline quinone. Reduced pyrrolo-quinoline quinone is usually more effective than oxidized pyrrolo-quinoline quinone. In vivo, it is believed that oxidized pyrrolo-quinoline quinone is reduced to become reduced pyrrolo-quinoline quinone. Reduced pyrrolo-quinoline quinone may be obtained, for example, by reducing oxidized pyrrolo-quinoline quinone using various reducing agents, such as sodium borohydride, sodium hyposulfite.

[Chem. 2]

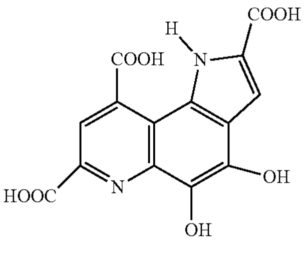

Pyrrolo-quinoline quinone may be prepared by extraction and purification from any source material or synthesized. Methods of manufacturing pyrrolo-quinoline quinone may include organic chemical methods, fermentation methods and the like. For example, bacteria that has a methanol assimilating property and a capability to produce pyrrolo-quinoline quinone may be manufactured by incubating them using methanol as a carbon source. Commercial products are available. For example, pyrrolo-quinoline quinone disodium salt is commercially available from MITSUBISHI GAS CHEMICAL COMPANY, INC.

In the sperm motility improvement agent of the present invention, the content of pyrrolo-quinoline quinone is not particularly limited. The amount of said sperm motility improvement agent to be used may be determined as appropriate by observing the effect, but in one embodiment, when semen with a sperm concentration (total sperm count) of $5\times10^6$ to $50\times10^6$/ml is as a standard, said sperm motility improvement agent is added so that the concentration of the pyrrolo-quinoline quinone is 20 to 200 nM, preferably 50 to 150 nM, more preferably 100 to 150 nM, based on said semen. When the concentration is less than 20 nM, the effect of the present invention may not be obtained, on the other hand, when the concentration exceeds 200 nM, the effect obtained is not so different and economically disadvantageous.

In one embodiment, the molar ratio of the nicotinamide mononucleotide to the pyrrolo-quinoline quinone in the sperm motility improvement agent of the present invention is 1:1 to 1500:1, preferably 1:1 to 1200:1, more preferably 1:1 to 1000:1. When the molar ratio is outside the range of 1:1 to 1500:1, the effect obtained by the present invention may be reduced.

A method for manufacturing the sperm motility improvement agent is not specifically limited, and a common manufacturing method applied for manufacturing the present agent according to its form may be selected as appropriate. For example, in a case of a powder form, the present agent can be manufactured by uniformly mixing nicotinamide mononucleotide and other components added in as necessary, such as pyrroloquinoline quinone. Note that, nicotinamide mononucleotide as an active ingredient is distributed in the market and is commercially available. Especially, in recent years, a quality management system and a mass production system of nicotinamide mononucleotide have been established, and the supply thereof is feasible.

The sperm motility improvement agent of the present invention can be used as a medicinal product (including a quasi-drug), a food and beverage product, and the like. A dosage form of the medicinal product is not specifically limited, but can include, for example, a powder, a tablet, a persistent tablet, a chewable tablet, an effervescent tablet, a troche, a buccal tablet, a sublingual tablet, a capsule formulation, a fine granule, a granule, a pill, a dry syrup, a liquid medicine, a suspending agent, a syrup, a formulation for oral administration such as an elixir, and an eye drop, an eyewash, an eye ointment, an injection preparation, a transfusion, and an external preparation. A dose of the medicinal product can be appropriately set in accordance with, for example, the type of the medicinal product, age, sex, and weight of a target that takes the medicinal product, the expected effect, and the symptom.

The medicinal product can appropriately contain a known additive for formulation, which is adequate for the dosage form and pharmacologically allowed, considering physicochemical property, biological property, and similar property. Such an additive for formulation is exemplified by, for example, an excipient (lactose, starch, crystalline cellulose, sodium phosphate, and the like), a solvent (water, soybean oil, saline solution, a nonaqueous solvent for injection, and the like), a binder (starch, gelatin, gum arabic, sodium alginate, carmellose sodium, methylcellulose, ethyl cellulose, hydroxypropyl methylcellulose, hydroxypropyl cellulose, polyvinylpyrrolidone, and the like), a disintegrant (starch, carmellose sodium, and the like), a lubricant (talc, magnesium stearate, calcium stearate, macrogol, sucrose fatty acid ester, and the like), a coating agent (white sugar, HPC, shellac, gelatin, glycerin, hydroxypropyl methylcellulose, hydroxypropyl methylcellulose phthalate, cellulose acetate phthalate, and the like), a stabilizer (sodium bisulfite, sodium thiosulfate, sodium edetate, sodium citrate, ascorbic acid, dibutylhydroxytoluene, and the like), a preservative (methyl parahydroxybenzoate, ethyl parahydroxybenzoate, propyl parahydroxybenzoate, benzyl alcohol, phenol, chlorobutanol, benzalkonium chloride, benzethonium chloride, sodium dehydroacetate, thimerosal, and the like), a viscous agent (methylcellulose, carmellose sodium, chondroitin sulfate, sodium alginate, and the like), a suspending agent (various nonionic surfactant, methylcellulose, carmellose sodium, and the like), an emulsifier (gum arabic, cholesterol, sorbitan sesquioleate, polysorbate 80, sodium lauryl sulfate, and the like), a buffer (citric acid, acetic acid, sodium phosphate, and boric acid), a surfactant (hydrogenated castor oil, polysorbate 80, and the like), a colorant (water-soluble food pigment, lake pigment, and the like), a corrigent (lactose, white sugar, glucose, mannitol, and the like), a scenting agent (aromatic essential oils), a plasticizer (the phthalic acid esters, vegetable oils, polyethylene glycol, and the like).

The sperm motility improvement agent of the present invention can be used as a food and beverage product (including a supplement), and the like. By daily ingesting the present agent in the form of a food product, the effect of the present invention can be provided repeatedly and is thus especially effectual for enjoying the effect even better. The type of the food product as the target of the present invention is not specifically limited, and the target includes a functional food, a food for specified health use, a dietary supplement, a food additive, a feed, a care food, a diet therapy food, a therapeutic diet, a diet food, and similar food product in addition to general food products. Specifically, for example, confectionery (gum, candies, cookies, gummi candies, biscuits, cakes, chocolates, Japanese confectionery, jelly, and the like), bread, noodles, rice/grain processed foods (cereals and the like), meat processed foods, fish and shellfish processed foods, vegetable processed foods, ready-prepared foods, fermented foods, seasonings (source, dressing, ketchup, and the like), spices, dairy products (yogurt, cheese, milk, and the like), ice cream, frozen foods, retort pouch foods, beverages (carbonated beverages, soft drinks, milk-based beverages, alcoholic beverages, sports beverages, fruit-flavored beverages, teas, nutritious beverages, concentrated beverages, and the like), powdered beverages (powdered juice, powdered soup, and the like) are exemplified. The form of the food product is not limited, and especially in the case of the functional food, the food for specified health use, and the like, the food product can be processed to be provided in the form of, for example, a powder, a tablet, a pill, a granule, a hard capsule formulation, a soft capsule formulation, a jelly, a liquid medicine, and a paste medicine. The intake of the food product can be appropriately set in accordance with, for example, the type of the food product, age, sex, and weight of a target that takes the food product, the expected effect, and the symptom.

The food product is safe and side effects are not specifically recognized. Therefore, the food product can be ingested over a long period of time. The food product can be applied to not only the elderly people but also the young people.

Another aspect of the present invention is a method of improving the sperm motility, comprising bringing nicotinamide mononucleotide in contact with sperm in vitro or in vivo. The sperm-derived biological species are not limited, but in one embodiment, examples include mammals, specifically humans, pigs, cattle, horses, sheep, goats, monkeys, rats, mice, rabbits, dogs, cats, and the like.

In addition, as mentioned in the sperm motility improvement agent of the present invention, the contact of pyrroloquinoline quinone with sperms in conjunction with nicotinamide mononucleotide may enhance the sustainability of the improving effect of nicotinamide mononucleotide on the sperm motion. The amounts of nicotinamide mononucleotide and pyrrolo-quinoline quinone to be applied and the like are as described above.

In the method of improving the sperm motility of the present invention, the method of bringing nicotinamide mononucleotide and, if necessary, pyrrolo-quinoline quinone into contact with sperms in vitro is not particularly limited. For example, this may be done by placing the target semen in a container, then adding nicotinamide mononucleotide and pyrrolo-quinoline quinone to the container and incubating for a predetermined time. The contact of nicotinamide mononucleotide and pyrrolo-quinoline quinone with sperms may be done multiple times by adding them again at predetermined time intervals. Besides, the both may be brought into contact, for example, by using an aqueous solution containing nicotinamide mononucleotide and pyrrolo-quinoline quinone as a diluent of semen.

In the method of improving the sperm motility of the present invention, the method of bringing nicotinamide mononucleotide and, if necessary, pyrrolo-quinoline quinone into contact with sperms in vivo is not particularly limited. For example, this may be done by injecting nicotinamide mononucleotide and pyrrolo-quinoline quinone together with sperms into the uterus of a mammal.

Sperms treated by the sperm motility improvement agent and the method of improving the sperm motility of the present invention have good sperm motility, especially forward motility, and are safe. The present invention is extremely useful in the fields of assisted reproductive technology, stockbreeding and the like, as it may lead to the improvement of asthenozoospermia, and thus to application in infertility treatment.

Working Example

Hereinafter, the present invention will be described in detail based on a working example, but the present invention is not limited by thereby.

Working Example (An Effect of Nicotinamide Mononucleotide (NMN) on the Sperm Motility)

(1) Method

Upon arrival of a pack containing swine diluted semen (sperm concentration (total sperm count) 30,000,000/ml, HIRO-SWINE B solution (HIROSHIMA CRYO-PRESERVATION SERVICE) was used as a diluent) provided by Oita Prefectural Agriculture, Forestry and Fisheries Research Center, the pack was immediately stored in an incubator at 15° C. The next day, 5 ml of the above semen from each pack was transferred to a 15 ml centrifuge tube, NMN was added to concentrations from 0.1 to 100 μM (0.1 μM, 1 μM, 10 μM, 100 μM) using HIRO-SWINE B solution as a culture medium, and they were incubated at 37° C. for up to 6 hours. For some diluted semen, pyrrolo-quinoline quinone (PQQ) (MITSUBISHI GAS CHEMICAL COMPANY, INC) was added to a concentration of 100 nM, in addition to NMN or without the addition of NMN, and it was incubated in the same manner. Sperms were taken out at 0, 2, 4, and 6 hours after the start of incubation, and their sperm motility was analyzed using CASA (HT CASA-Ceros II (product name), Hamilton Thorne, Inc.). For the sperm motility, the total moment (%), which is the proportion of the number of sperms in motion to the total number of sperms counted, the straight (forward) moment (%), which is the proportion of the number of sperms in straight (forward) motion to the number of sperms in motion, and the straight (forward) speed (μm/s) of the sperms in straight (forward) motion were analyzed and these results were shown in FIGS. 2*a*, 2*b* and 2*c* respectively. The error bars in FIG. 2 represent standard errors. Sperm motion loci were also photographed by phase contrast microscopy at 2, 4, and 6 hours after the start of incubation and the photographs were shown in FIG. 3.

(2) Results

The total moment was not affected by different concentrations of NMN addition (FIG. 2*a*). However, the straight moment and the straight speed in the straight motion of sperms, which is essential for sperms to ascend in the genital tract, were significantly increased in the NMN alone addition zone (PQQ−), and the effect was observed up to 4 hours later (FIG. 2*b*, FIG. 2*c*, FIG. 3). However, in the NMN alone addition zone, the improving effect of the NMN alone addition on the straight moment and the straight speed disappeared 6 hours later (FIG. 2*b*, FIG. 2*c*, FIG. 3). On the other hand, in the combined addition zone with PQQ (PQQ+), the effect of adding NMN and PQQ was observed from lower concentrations (0.1 μM and 1 μM) (4 hours later) and the effect sustained up to 6 hours later (FIG. 2*b*, FIG. 2*c*, FIG. 3).

(3) Discussion

The above experimental results confirm that NMN is utilized by sperms and that NMN has the effect of enhancing the straight moment and the straight speed of sperms. In addition, the further addition of PQQ enhances the sustainability of the effect of NMN, confirming that the combined treatment with PQQ is effective. Although the straight motion of sperms was enhanced in the NMN alone addition zone, the effect was not sustained for a long period of time, according to the experimental results, in which the addition of PQQ imparted a sustained effect, in the mechanism by which the action effects of the present invention are brought about, as described above, the contact of NMN with sperms increases the amount of NAD/NADH in sperm, activates the electron transfer system, increases ATP concentration in mitochondria, and enhances the sperm motility, however at this time active oxygen are also generated, which inhibit the effect sustainability of NMN, and when PQQ is added, it was estimated that the effect of NMN is prolonged because PQQ blocks the action of reactive oxygen.

The invention claimed is:

1. A method of improving sperm motility, comprising bringing nicotinamide mononucleotide and pyrrolo-quinoline quinone in contact with semen ex vivo.

2. The method according to claim 1 wherein the semen is a mammalian semen.

3. The method according to claim 1, comprising adding the nicotinamide mononucleotide to semen with a sperm concentration of $5\times10^6$ to $50\times10^6$/ml such that a concentration of the nicotinamide mononucleotide becomes 0.05 to 150 μM.

4. The method according to claim 1, comprising adding the pyrrolo-quinoline quinone to semen with a sperm concentration of $5\times10^6$ to $50\times10^6$/ml such that a concentration of the pyrrolo-quinoline quinone becomes 20 to 200 nM.

5. The method according to claim 1, wherein a molar ratio of the nicotinamide mononucleotide to the pyrrolo-quinoline quinone is 1:1 to 1500:1.

6. A semen sperm treated by the method according to claim 1.

* * * * *